United States Patent
Chelak et al.

(10) Patent No.: US 11,565,084 B2
(45) Date of Patent: Jan. 31, 2023

(54) LOW PROFILE CATHETER SYSTEM

(71) Applicant: NP Medical Inc., Clinton, MA (US)

(72) Inventors: Todd Chelak, Westborough, MA (US); Ian Kimball, Lunenburg, MA (US); Luis Maseda, Natick, MA (US); Jonathan Gabel, Randolph, NJ (US)

(73) Assignee: NP Medical Inc., Clinton, MA (US)

( * ) Notice: Subject to any disclaimer, the term of this patent is extended or adjusted under 35 U.S.C. 154(b) by 160 days.

(21) Appl. No.: 16/864,374

(22) Filed: May 1, 2020

(65) Prior Publication Data

US 2021/0338986 A1 Nov. 4, 2021

(51) Int. Cl.
*A61M 25/02* (2006.01)
*A61M 25/00* (2006.01)
*A61M 39/24* (2006.01)

(52) U.S. Cl.
CPC ........ *A61M 25/02* (2013.01); *A61M 25/0097* (2013.01); *A61M 39/24* (2013.01); *A61M 2025/0266* (2013.01); *A61M 2039/242* (2013.01)

(58) Field of Classification Search
CPC .. A61M 25/02; A61M 25/00; A61M 25/0625; A61M 25/0606; A61M 25/06; A61M 25/0097; A61M 2025/028; A61B 5/150969
See application file for complete search history.

(56) References Cited

U.S. PATENT DOCUMENTS

| | | | | |
|---|---|---|---|---|
| 6,056,718 A | * | 5/2000 | Funderburk | A61M 25/0097 604/161 |
| 6,123,690 A | * | 9/2000 | Mejslov | A61M 39/14 604/533 |
| 6,224,571 B1 | * | 5/2001 | Bierman | A61M 25/02 604/174 |
| 10,537,714 B2 | | 1/2020 | Andino et al. | |
| 2005/0215979 A1 | * | 9/2005 | Kornerup | A61M 37/00 604/93.01 |

(Continued)

FOREIGN PATENT DOCUMENTS

CN 109069818 A 12/2018
KR 10-1830593 B1 2/2018

OTHER PUBLICATIONS

International Search Report and Written Opinion for Application No. PCT/US2021/027743, dated Aug. 5, 2021, 6 pages.

*Primary Examiner* — Bhisma Mehta
*Assistant Examiner* — Robert F Allen
(74) *Attorney, Agent, or Firm* — McCarter & English, LLP; Jonathan C. Lovely

(57) ABSTRACT

A low profile catheter system includes a catheter hub with a stabilization surface that is located on an underside of the catheter hub and stabilizes the catheter hub on a patient. A substantially linear flow path extends from an opening at the distal end of the catheter hub to an inlet located within an intermediate portion of the catheter hub. The flow path allows fluid to flow between the distal end and the intermediate portion. The intermediate portion receives a base connector having a fluid path. The fluid path has a first opening and is fluidly connected to the inlet of the flow path in the catheter hub and a biasing member biases the first opening toward the inlet when the base connector is received by the intermediate portion.

17 Claims, 11 Drawing Sheets

(56) References Cited

U.S. PATENT DOCUMENTS

| | | | |
|---|---|---|---|
| 2006/0030815 A1 | 2/2006 | Csincsura et al. | |
| 2010/0234820 A1* | 9/2010 | Tsai | A61M 1/87 |
| | | | 604/385.03 |
| 2010/0298777 A1* | 11/2010 | Nishtala | A61M 39/10 |
| | | | 604/174 |
| 2015/0051584 A1* | 2/2015 | Korkuch | A61M 25/0606 |
| | | | 604/95.01 |
| 2015/0320976 A1* | 11/2015 | Maseda | A61M 39/24 |
| | | | 604/180 |
| 2016/0121046 A1 | 5/2016 | Wyss et al. | |
| 2018/0289920 A1* | 10/2018 | Harding | A61M 25/0082 |
| 2019/0275312 A1* | 9/2019 | Chelak | A61M 39/0247 |
| 2020/0324101 A1* | 10/2020 | Hartmann | A61M 39/105 |

* cited by examiner

LOW PROFILE CATHETER SYSTEM

TECHNICAL FIELD

The present invention relates to vascular access sites, and more particularly to low profile catheter systems that allow a user to easily connect and disconnect from a catheter inserted into a patient's vasculature.

BACKGROUND ART

In instances in which a patient will need regular administration of fluid or medications (or regular withdrawal of fluids/blood), catheters are often inserted into the patient and used to administer the fluids/medications. The catheter may remain in the patient for extended periods of time (several hours to several days or longer). Additionally, an extension tube may be connected to the catheter to facilitate use of the catheter and connection of a medical implement (e.g., a syringe). To ensure that the catheter and/or extension tube remain in place and are not accidentally removed, some prior art systems secure the catheter and/or extension tube to the patient using tape or similar adhesive materials (e.g., a film dressing).

Typical peripheral IV Catheters in the market today possess inlet hubs that utilize ISO 80369-7 Luer connections. These tubular connections are cumbersome for the user to manipulate (often leading to incomplete connections), and they force undesirable profiles that create snag hazards. Additionally, the associated components are uncomfortable pressure points when resting on the skin of patients during the episode of care.

SUMMARY OF THE INVENTION

In accordance with one embodiment of the invention, a low profile catheter system may include a catheter hub, a base connector and a biasing member. The catheter hub may have a proximal end, a distal end and a stabilization surface located on an underside of the catheter hub. The stabilization surface may stabilize the catheter hub on a patient. The catheter hub may also have a substantially linear flow path extending from an opening at the distal end to an inlet located within an intermediate portion of the catheter hub. The flow path may allow fluid to flow between the distal end and the intermediate portion of the catheter hub, and the inlet may be located between the proximal end and the distal end of the catheter hub. The base connector may have a fluid path extending through at least a portion of the base connector, and the intermediate portion of the catheter hub may receive the base connector. The fluid path may have a first opening and may be fluidly connected to the inlet of the flow path in the catheter hub when the base connector is received by the intermediate portion of the catheter hub. The biasing member may bias the first opening of the fluid path toward the inlet when the base connector is received by the intermediate portion of the catheter hub.

In some embodiments, the catheter system may also include a catheter that is at least partially secured within and extending into the flow path. At least a portion of the underside may include a flat surface, and the catheter may have a longitudinal axis that is oriented at an angle with respect to the flat surface. Additionally or alternatively, the system may include an introducer that is removably connectable with the catheter hub when the base connector is not connected. The introducer may have a handle and a needle configured to extend through the flow path and catheter when the introducer is connected.

In accordance with further embodiments, the catheter hub may have a fluid seal interface around the inlet of the flow path, and the biasing member may axially bias the first opening of the fluid path toward the fluid seal interface. Additionally or alternatively, the base connector may include a sealing member located at the first opening. The sealing member may seal against the fluid seal interface when axially biased toward the fluid seal interface. The biasing member may be located on the catheter hub.

The low profile catheter system may also include a first retention feature located on the catheter hub and a second retention feature located on the base connector. The first and second retention features may interact with one another to secure the base connector to the catheter hub when the base connector is received by the intermediate portion of the catheter hub. In some embodiments, the catheter hub may have a recess located within a top surface of the catheter hub and at least within the intermediate portion. The recess may be configured to receive at least a portion of the base connector. The catheter hub may also have at least one indent and the base connector may include at least one projection extending from it. The projection(s) may enter the indent(s) in the catheter hub upon receiving the base connector to align the base connector within the catheter hub. The catheter hub may include least one slot extending through it to provide access to the patient's skin.

In accordance with additional embodiments, the base connector may include a valve mechanism (e.g., a two-way pressure activated valve) that controls fluid flow through the fluid path. A bottom surface of the base connector may include a recess that, in turn, houses at least one sensor. To help stabilize and/or secure the catheter hub to/on the patient, the system may include an adhesive layer located on the stabilization surface. The catheter hub may have at least one projection that extends from a surface of the catheter hub and the base connector may have at least one recess. The projection(s) may enter the recess(es) when the base connector is received by the catheter hub to secure the base connector to the catheter hub.

In some embodiments, the system may include a tube connected to a second opening of the fluid path and/or a dressing secured to the base connector. The dressing may be configured to secure the catheter system to the patient. For example, the dressing may include a patch layer secured to a top surface of the base connector, and the patch layer may have a securement portion extending beyond the top surface of the base connector that adheres to the patient. The dressing may also have a first, second and third film layer. The first film layer may be located at least partially on the patch layer and may have an opening nearer a first end of the first film layer. The second film layer may be located on the first film layer and may have a channel extending along at least a portion of its length. The third film layer may be located on the second film layer. The first, second and third film layers, the opening in the first film layer, and the channel may form a fluid pathway that is in fluid communication with the fluid path within the base connector.

In accordance with further embodiments of the present invention, a method for transferring fluid to and/or from a patient includes providing a low profile catheter system that has a catheter hub, a base connector, and a biasing member. The catheter hub may have a proximal end, a distal end and a stabilization surface located on an underside of the catheter hub. The catheter hub may also have a substantially linear flow path extending from an opening at the distal end to an inlet located within an intermediate portion of the catheter hub. The flow path may allow fluid to flow between the distal end and the intermediate portion of the catheter hub. The inlet may be located between the proximal end and the distal end of the catheter hub. The base connector may have a fluid path extending through at least a portion of it, and the intermediate portion of the catheter hub may receive the base connector. The fluid path has a first opening and may be fluidly connected to the inlet of the flow path in the catheter hub when the base connector is received by the intermediate portion of the catheter hub. The biasing member may bias the first opening of the fluid path toward the inlet when the base connector is received by the intermediate portion of the catheter hub.

The method may also include fluidly connecting the flow path within the catheter hub with the patient's vasculature and placing the catheter hub on the patient such that the stabilization surface stabilizes the catheter hub on the patient. The method may then connect the base connector to the catheter hub such that the intermediate portion of the catheter hub receives the base connector. The biasing member may then bias the first opening of the fluid path toward the inlet to fluidly connect to the flow path and the fluid path when the base connector is received by the intermediate portion of the catheter hub. The method may then transfer fluid to and/or from the patient through the flow path and the fluid path.

In some embodiments, the catheter hub may include a catheter at least partially secured within and extending into the flow path, and fluidly connecting the fluid path with the patient's vasculature and may include inserting the catheter into the patient's vasculature. For example, fluidly connecting the fluid path with the patient's vasculature may include connecting an introducer to the catheter hub prior to connecting the base connector. The introducer may have a needle that extends through the flow path and the catheter when the introducer is connected. The method may then insert the needle into the patient's vasculature, thereby inserting the catheter into the patient's vasculature, and disconnect the introducer from the catheter hub.

The catheter hub may have a fluid seal interface around the inlet of the flow path, and the biasing member may axially bias the first opening of the fluid path toward the fluid seal interface. Additionally or alternatively, the base connector may have a sealing member located at the first opening. The sealing member may seal against the fluid seal interface when axially biased toward the fluid seal interface. To secure the base connector to the catheter hub, the catheter hub may have a first retention feature and the base connector may have a second retention. The first and second retention feature may interact with one another to secure the base connector to the catheter hub when the base connector is received by the intermediate portion of the catheter hub. To receive at least a portion of the base connector, the catheter hub may have a recess located within a top surface within the intermediate portion.

In other embodiments, the catheter hub may also have at least one indent and the base connector may have at least one projection extending from it. In such embodiments, connecting the base connector to the catheter hub may include inserting the projection(s) into indent(s) in the catheter hub. The base connector may have a valve mechanism that controls fluid flow through the fluid path. The system may have an adhesive layer located on the stabilization surface to secure the catheter hub to the patient when the catheter hub is placed on the patient and/or a dressing secured to the base connector. The method may then apply the dressing to the patient to secure the catheter system to the patient. The dressing may include a film based fluid pathway fluidly connected to the fluid path.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

In illustrative embodiments, a low profile catheter system includes a catheter hub with a stabilization surface that stabilizes the system on the patient and a linear flow path extending through a portion of the catheter hub. The flow path allows fluid to flow between a distal end and an intermediate portion of the catheter hub. The intermediate portion of the catheter hub may receive a base connector having a fluid path extending through a portion of it. When the connector is received by the catheter hub, an opening of the fluid path is fluidly connected to the inlet of the flow path in the catheter hub and a biasing member biases the first opening of the fluid path toward the inlet. Details of illustrative embodiments are discussed in greater detail below.

Figure 1:
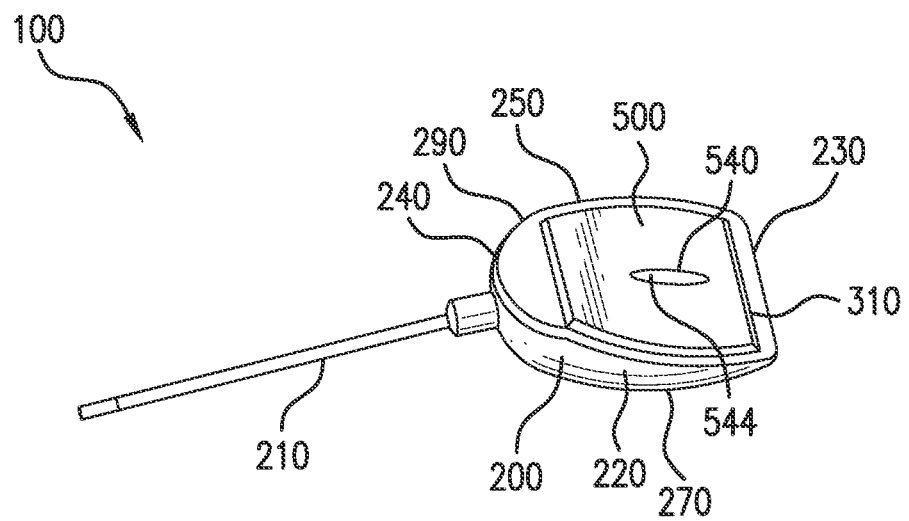
FIG. 1 schematically shows a perspective view of a low profile catheter system, in accordance with some embodiments of the present invention.
Figure 2:
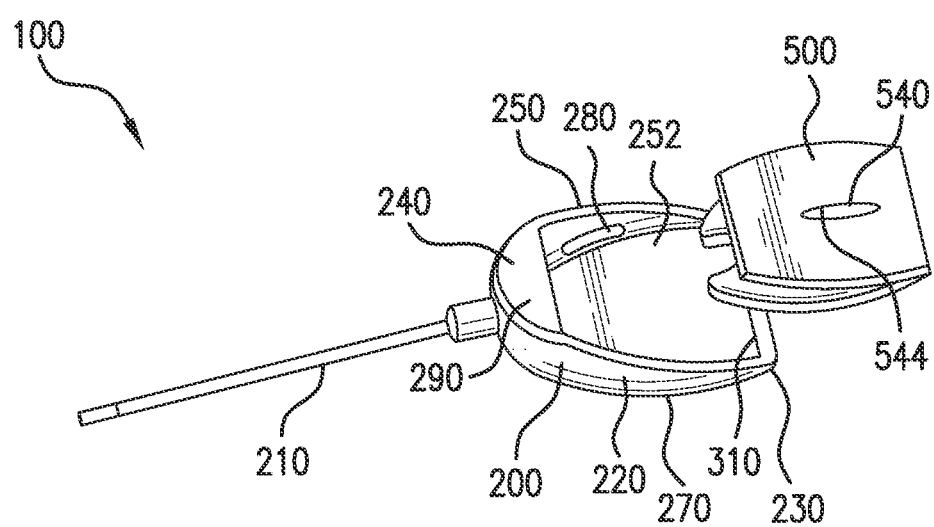
FIG. 2 schematically shows the low profile catheter system of FIG. 1 with a base connector disconnected from a catheter hub, in accordance with various embodiments of the present invention.

FIGS. 1 and 2 schematically show a low profile catheter system 100 that includes a catheter hub 200 and a base connector 500 that may be connected to (e.g., received by) the catheter hub 200 (FIG. 1) and disconnected/removed from the catheter hub 200 (FIG. 2). As discussed in greater detail below, the catheter hub 200 may include a catheter 210 that may be inserted into the patient's vasculature (e.g., into a vein of the patient). When the base connector 500 is connected to the catheter hub 200, a user can transfer fluids to and/or from a patient, even in high pressure applications.

As shown in FIGS. 3-7, the catheter hub 200 has a hub body 220 with a proximal end 230, a distal end 240 and an intermediate portion 250 located between the proximal end 230 and the distal end 240. Extending through a portion of the hub body 220 (e.g., between the distal end 240 and the intermediate portion 250), the catheter hub 200 may have a flow path 260 (e.g., a linear flow path) that allows fluid to flow through the catheter hub 200. To stabilize the catheter hub 200 (and the catheter system 100) on the patient, the catheter hub 200 may have a stabilization surface 270 located on an underside of the hub body 220. To help secure the device 100 to the patient, the stabilization surface 270 may have an adhesive layer (not shown) that adheres the catheter hub 200 to the patient.

The intermediate portion 250 of the catheter hub 200 may include a recess 252 that receives the base connector 500 during connection of the base connector 500 and the catheter hub 200. To help align the base connector 500 within the catheter hub 200, the catheter hub 200 (e.g., the intermediate portion 250) may have one or more indents 254 that receive one or more guidance tabs 520 extending from the body 510 of the base connector 500 (discussed in greater detail below). Additionally, to secure the base connector 500 within the intermediate portion 250 of the catheter hub 200, the catheter hub 200 may have one or more snap tabs 280 that extend into the recess of the intermediate portion 250 and enter a snap retention feature 530 (e.g., a snap recess) within the base connector 200. Alternatively, the base connector 200 may have one or more snap tabs that enter retention features on the catheter hub during connection. It should be noted that although two snap tabs 280 and two retention features 530 are shown, other embodiments may have more or less snap tabs and retention features and/or the catheter hub 200 and base connector 500 may each have both snap tabs and retention features.

Figure 3:
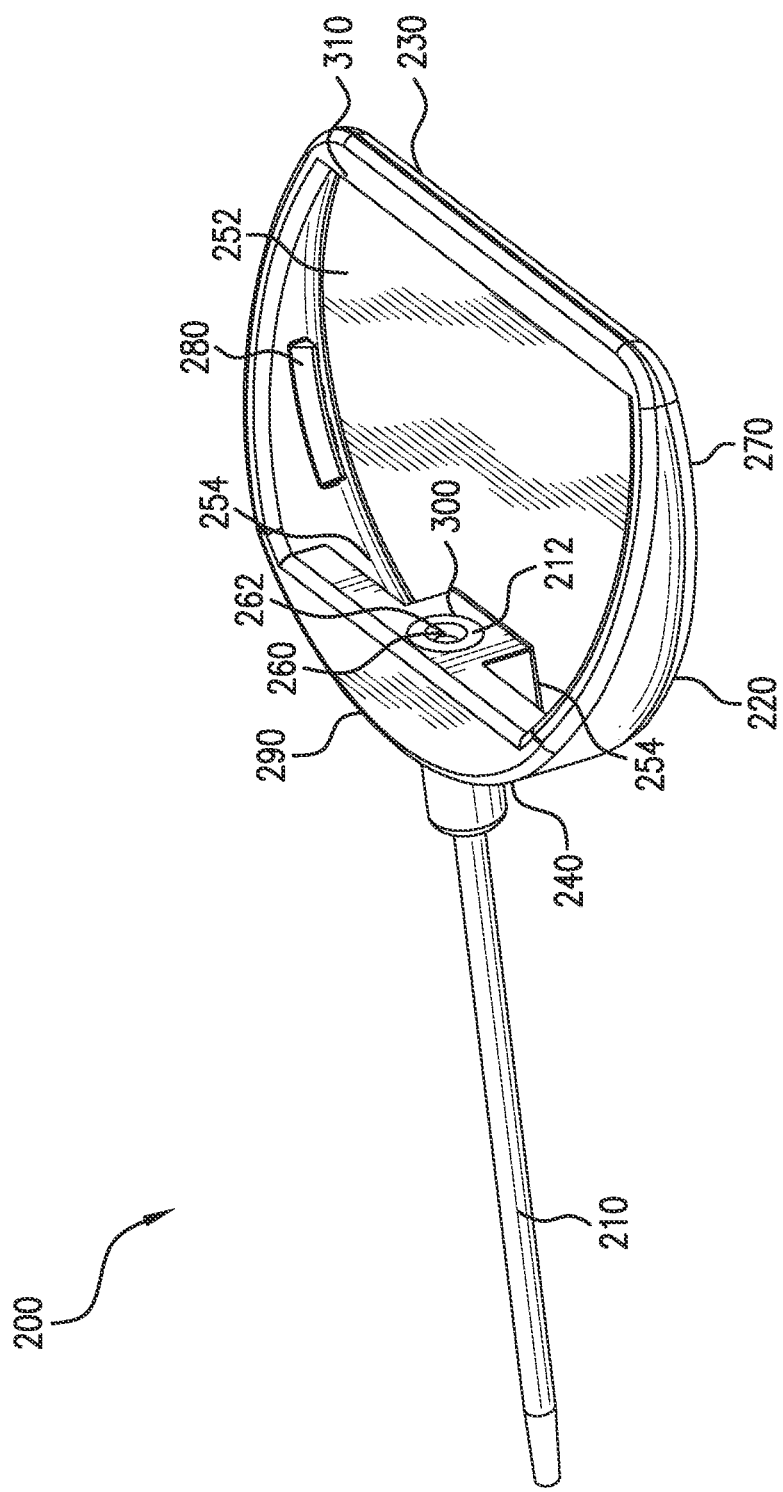
FIG. 3 schematically shows a perspective view of the catheter hub, in accordance with some embodiments of the present invention.
Figure 4:
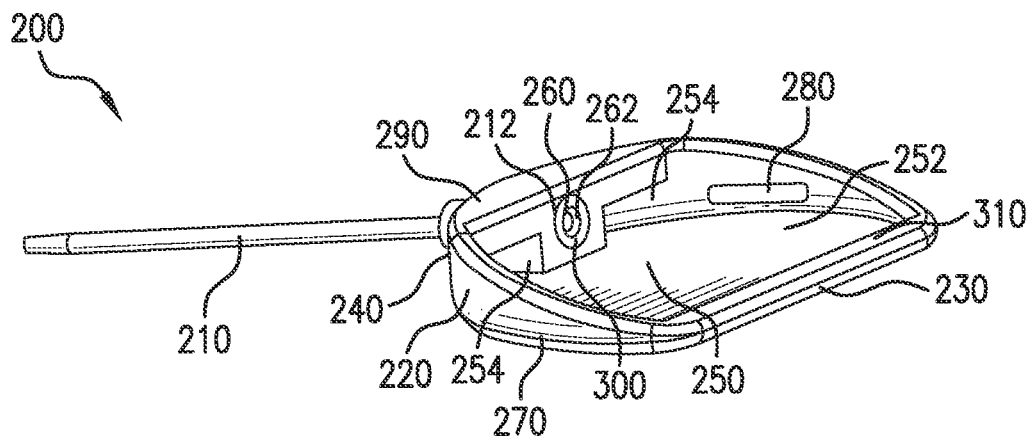
FIGS. 4-7 schematically show back, top, side and front views of the catheter hub shown in FIG. 3, in accordance with various embodiments of the present invention.
Figure 5:
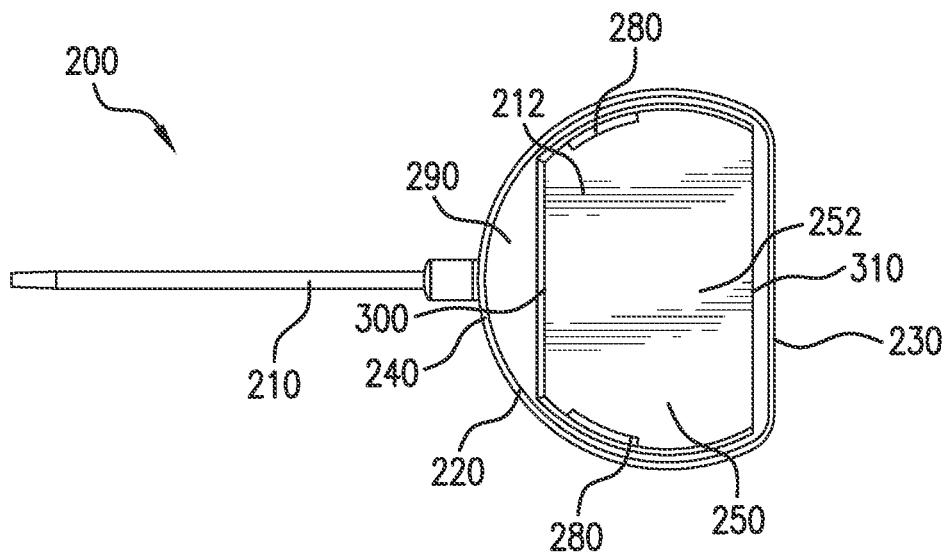
Figure 6:
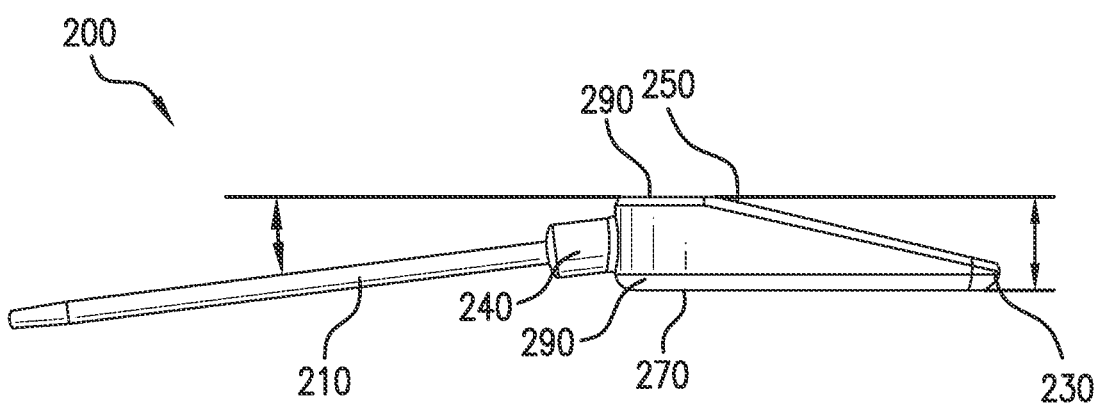
Figure 7:
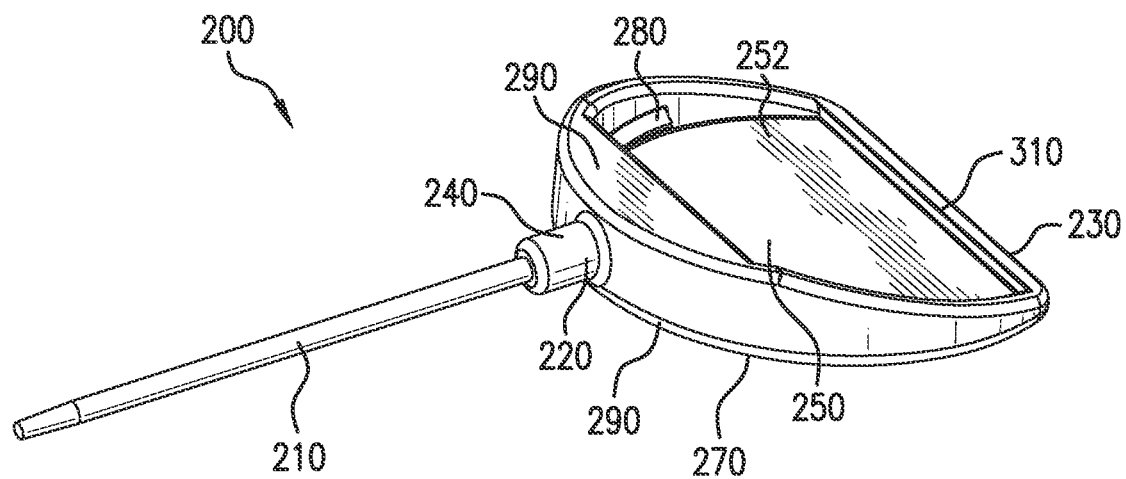

As best shown in FIGS. 3 and 4, the catheter 210 may extend either partially or entirely through and may be secured within the flow path 260. Additionally or alternatively, to minimize the pressure/force/strain on the insertion site of the patient and preserve the insertion angle of the catheter 210, the flow path 260 and/or the catheter 210 may be oriented at an angle with respect to the catheter hub 200. For example, the catheter hub 200 may have a flat surface 290 located on a top and/or bottom surface and the longitudinal axis of the catheter 210 and/or the flow path 260 may be oriented at an angle (e.g., 7 degrees) with respect to the flat surface 290.

Figure 13:
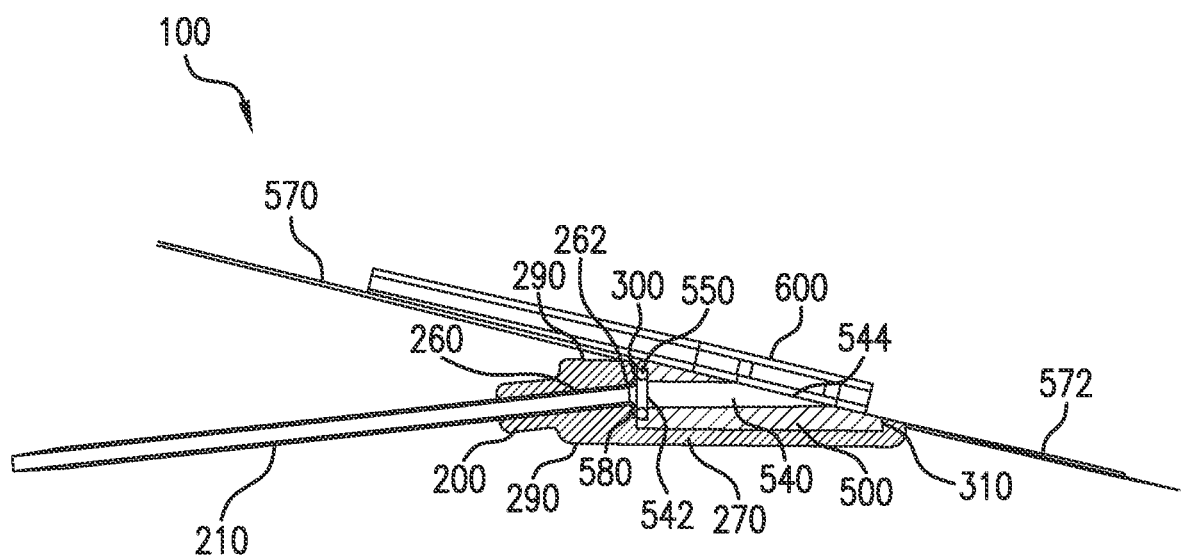
FIGS. 13-14 schematically show a cross sectional view and cross sectional close-up view of the catheter system with the base connector connected to the catheter hub, in accordance with various embodiments of the present invention.
Figure 14:
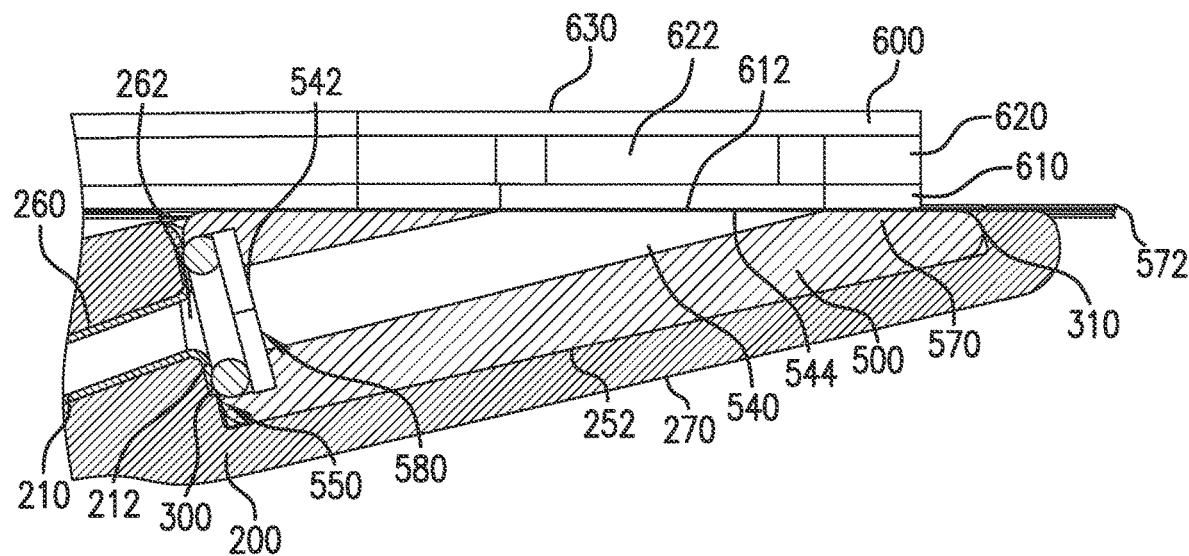
Figure 15:
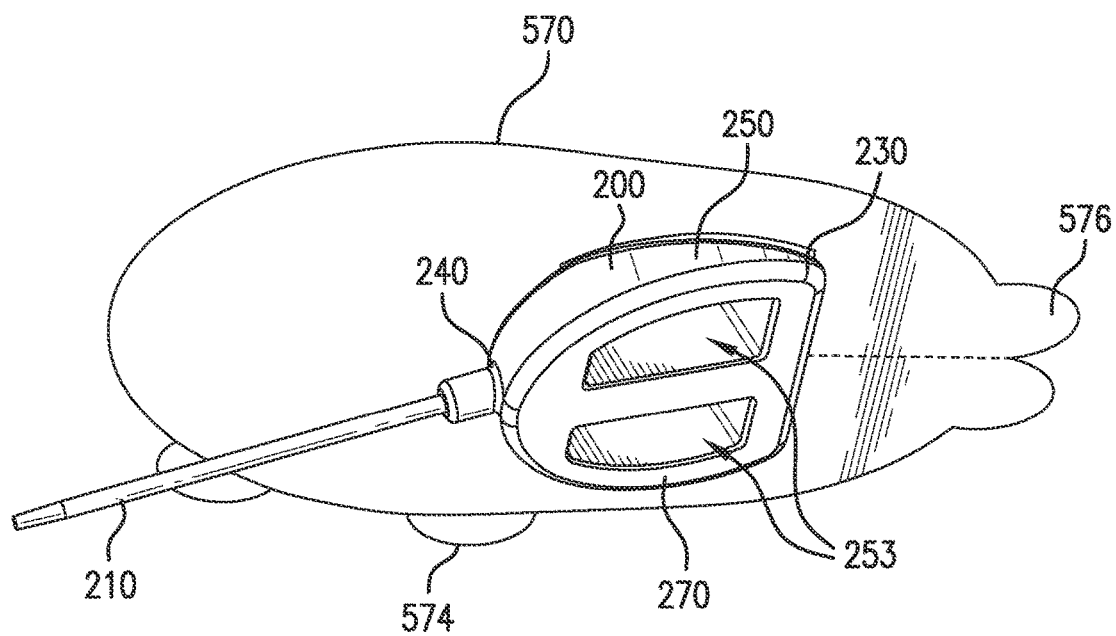
FIGS. 15-16 schematically show a bottom view and a top view of the catheter system with the base connector connected to the catheter hub, in accordance with various embodiments of the present invention.
Figure 16:
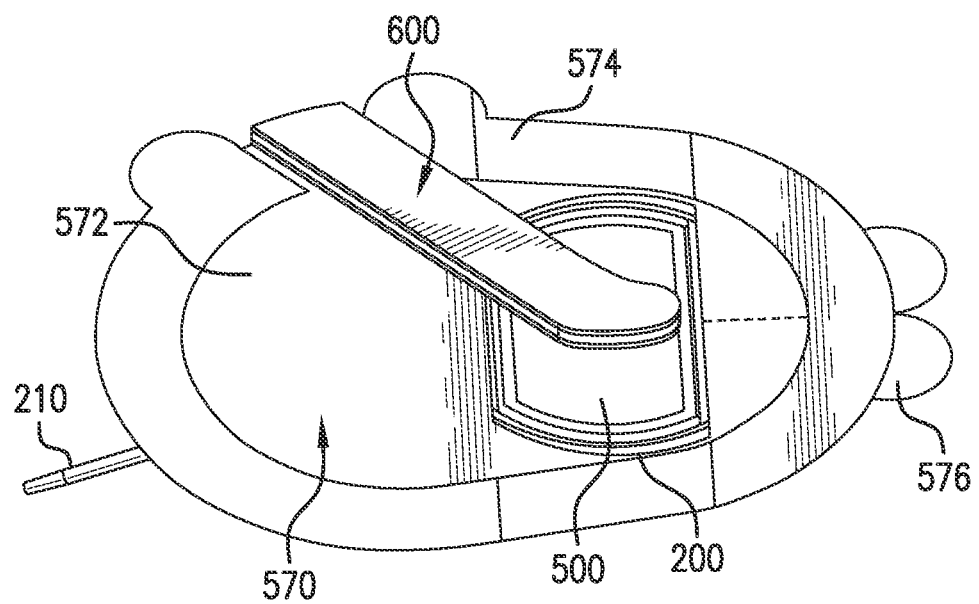
Figure 17:
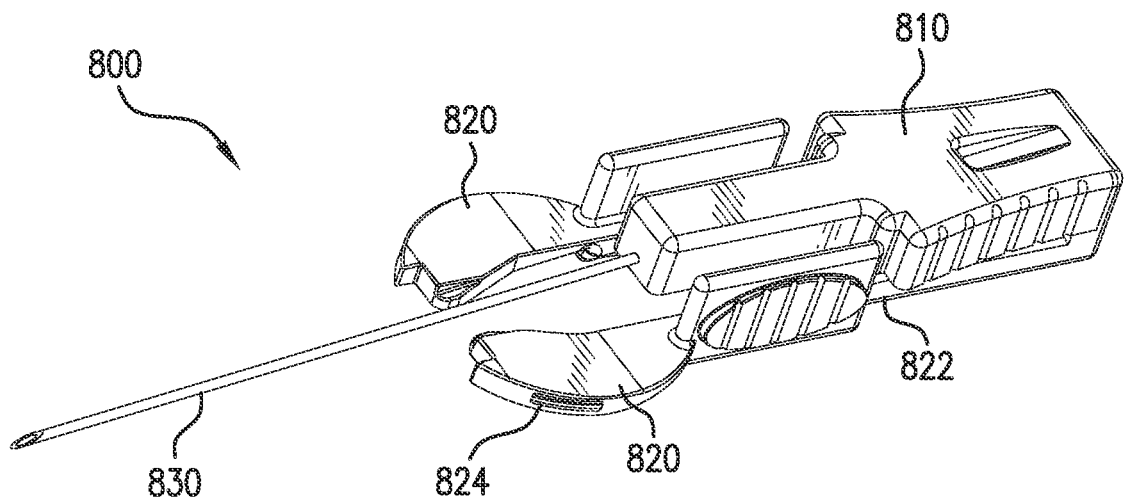
FIG. 17 schematically shows an introducer used to insert the catheter into the patient's vasculature, in accordance with some embodiments of the present invention.

As discussed in greater detail below, the flow path 260 within the catheter hub 200 fluidly connects to a fluid path 540 within the base connector 500 when the base connecter 500 is connected. To that end, the catheter hub 200 may include a fluid seal interface 300 located around the inlet 262 of the flow path and against which the fluid path 540 within the base connector 500 and/or a sealing element 550 within the base connector 500 may seal. The fluid seal interface 300 may be a surface on the intermediate portion 250 or it may be a flared portion 212 of the catheter 210 (FIGS. 13 and 14).

Additionally, to ensure a tight seal between the fluid path 540/sealing element 550 and the fluid seal interface 300, the catheter hub 200 may include a biasing element 310 that contacts the base connector 500 when connected and biases the base connector 500 toward the distal end 240 and the first opening 542 toward the fluid seal interface 300. For example, the biasing element 310 may be a curved stepped feature that creates longitudinal dimensional interference with base connector 500 thereby pushing the base connector 500 toward the distal end 240 of the hub 200 while intermediate portion 250 flexes to receive base connector 500 and/or fluid seal interface 300 and/or sealing element 550 compresses. Alternatively, the hub 200 may be at least partially an elastomeric member that stretches open to receive the base connector 500. In such embodiments, the elastomeric nature of the rear wall of the hub 200 (e.g., the wall at the proximal end 230) will bias the base connector 500 toward the distal end 240.

Figure 8:
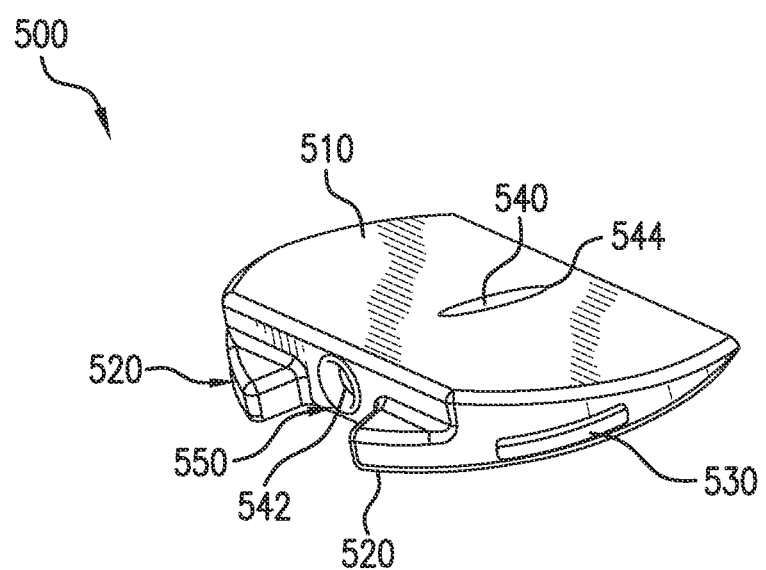
FIG. 8 schematically shows a perspective view of the base connector, in accordance with some embodiments of the present invention.

As noted above and as shown in FIG. 8, the base connector 500 may have one or more projections or guidance tabs 520 extending from the connector body 510 that help align the base connector 500 within the catheter hub 200 during connection. It should be noted that, in addition to performing this guidance/alignment function, the projections 520 may also help to prevent contamination of the sealing element 550 (e.g., an O-ring) and/or the opening 542 of the fluid path 540. For example, because these projections 520 extend out further than the sealing element 550 and extend beyond the opening 542, the projections 520 will prevent contamination if the user accidentally bumps the base connector 500 against a surface (e.g., because the projections 520 will prevent the sealing element 550 and/or the opening 542 from contacting the surface).

Figure 9:
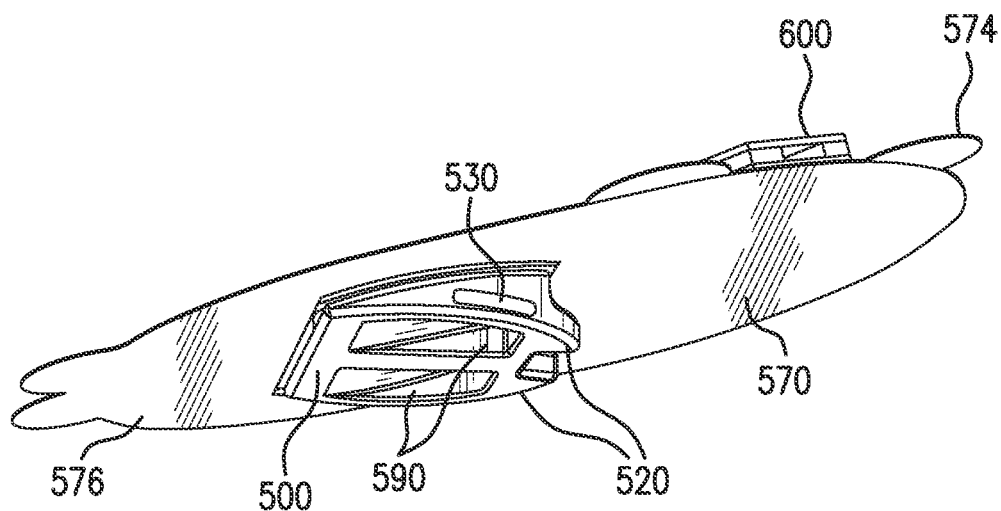
FIGS. 9-11 schematically show a bottom, top and exploded view of an alternative base connector with a dressing portion and film based fluid pathway, in accordance with some embodiments of the present invention.
Figure 10:
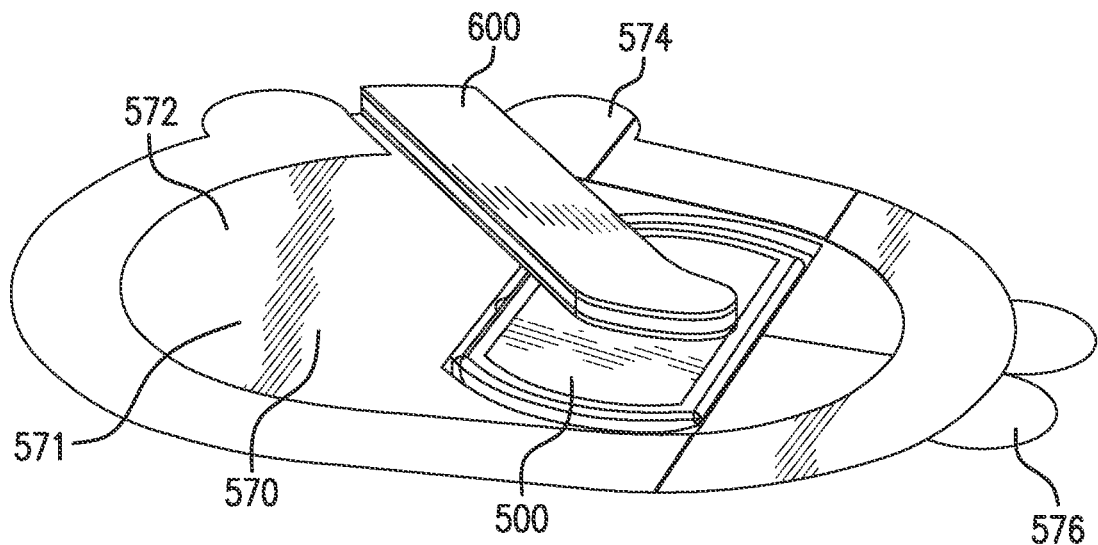
Figure 11:
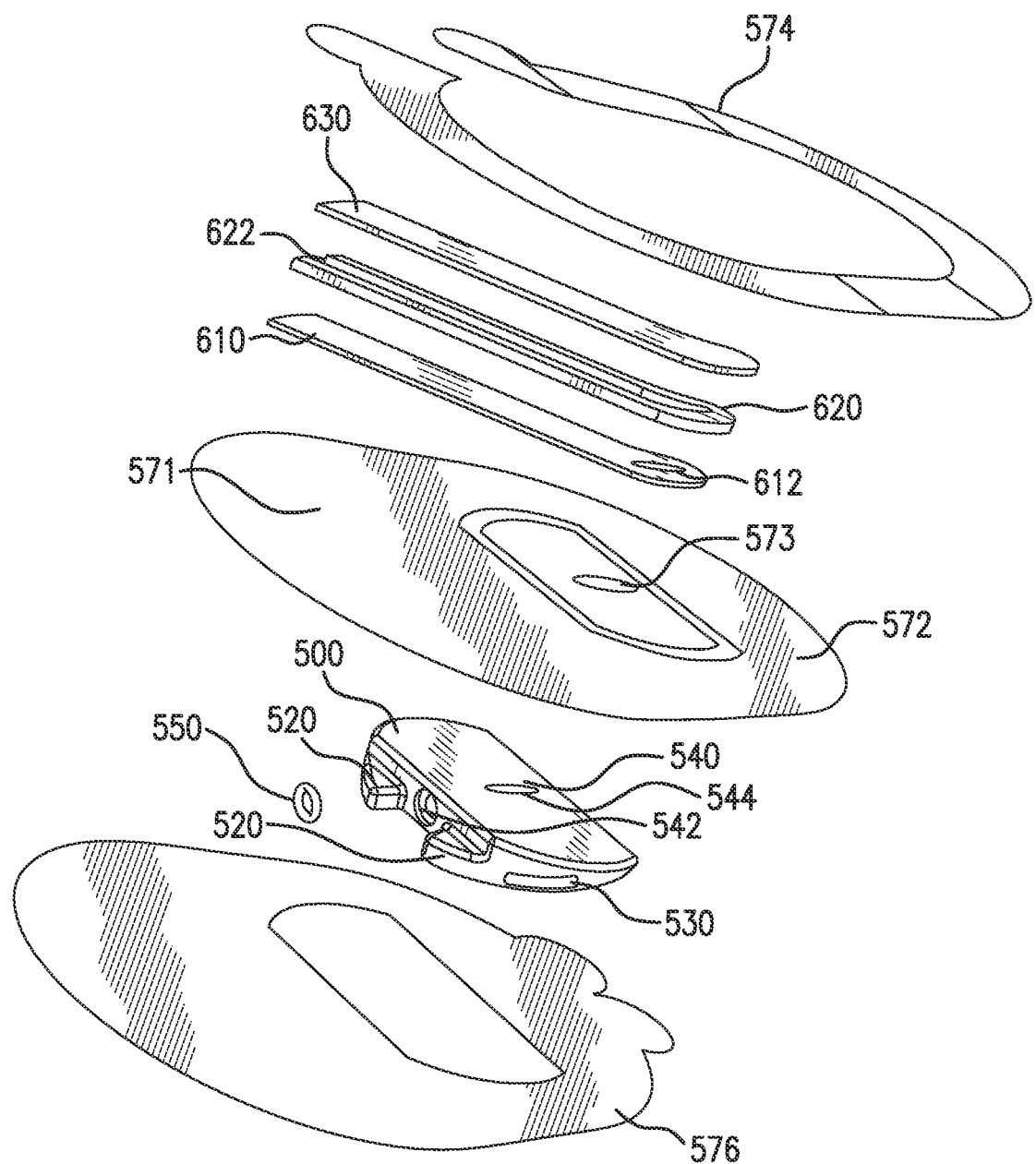

To help secure the catheter system 100 to the patient and help protect the catheter insertion site (e.g., by providing and environmental barrier), the base connector 500 may have a dressing 570 (e.g., a patch) secured to the body 510 of the base connector 500 (e.g., via adhesive, ultrasonic welding, RF welding, laser welding or similar securement method). As shown in FIGS. 9-11, the dressing 570 may include a number of layers. For example, the dressing 570 may include a patch layer 572 that includes an adhesive located on an underside of the patch layer 572, a dressing frame 574 that provides some structural rigidity to the dressing 570, and a release liner 576 that covers and protects the adhesive on the patch layer 572 prior to use. The patch layer 572 may have a securement portion 571 that extends beyond the base connector 500 and contacts the skin of the patient to secure the dressing 570 and device 100 to the patient. The patch layer 572 may include an opening 573 that provides access to the fluid path 540 in the base connector 500. During use, the user may remove the release liner 576 to expose the adhesive on the patch layer 572, grasp the dressing 570 by the dressing frame 574 (e.g., tabs on the dressing frame 574) and may position the dressing over the catheter insertion site, causing the adhesive and the securement portion 571 to adhere to the skin.

The bottom surface of the base connector 500 may include one or more recesses 590 that house sensors, electronics, or other technologies that may be used to sense, analyze or detect a characteristic of a patient. Alternatively, the electronics/sensors may be printed directly onto the bottom surface of the base connector 500. In such embodiments, the intermediate portion 250 of the catheter hub 200 may have one or more corresponding openings 233 in the recess 252 to provide access to the patient's skin. In addition to providing the sensors/electronics access to the skin, these openings 253 may also help to facilitate skin moisture transmission.

Figure 12:
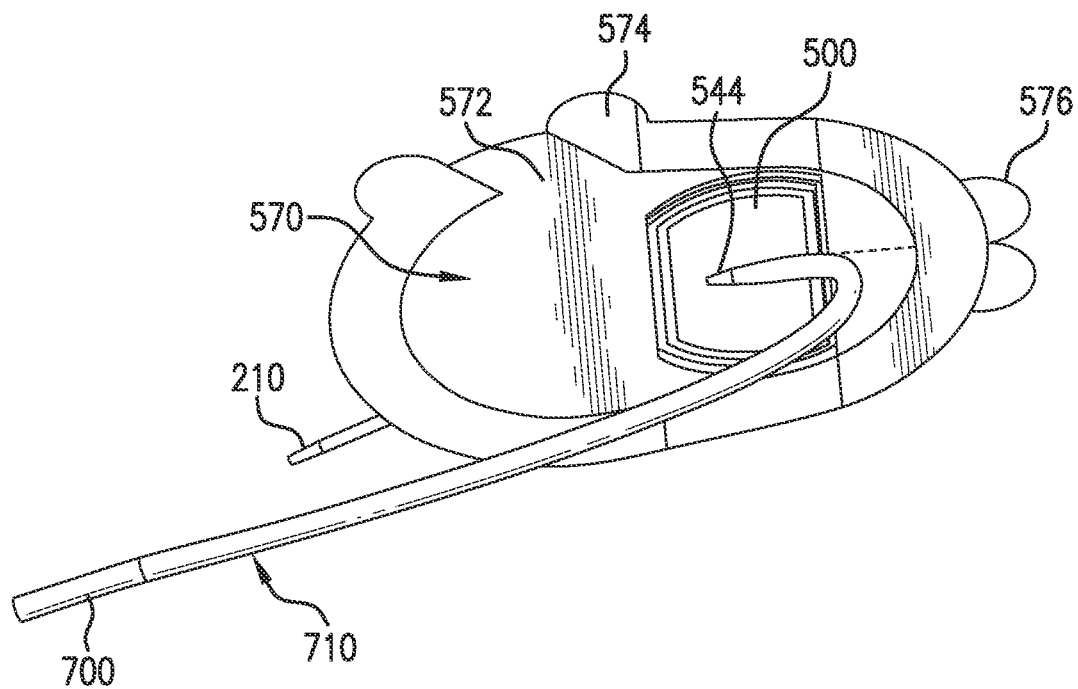
FIG. 12 schematically shows an alternative embodiment of the base connector with a dressing and a tube, in accordance with various embodiments of the present invention.

To facilitate fluid flow through the catheter system 100, the base connector 500 may include and/or may be connected to any number of extension sets, tubes, or fluid transfer devices. For example, the base connector 500 (e.g., the second opening 544 of the fluid path 540 through the base connector) may include or be connected to a film based fluid pathway/extension set 600 (FIGS. 9-11) or a standard/tube based extension set 700 (FIG. 12) or a female luer connector (not shown). For the standard/tube based extension set 700, one end of the tube 710 may be fluidly connected to/secured to the fluid path at the second opening 544 and fluid may be transferred to and/or from the patient via the tube 710, the fluid path 540 through the base connector 500, the flow path 260 through the catheter hub 200, and the catheter 210.

As the name suggests, the film based fluid path 600 may be formed from multiple layers of film that define a fluid path extending through at least a portion of the layers. For example, the film based fluid path 600 may have a lower layer 610, a middle layer 620 and a top layer 630. The lower layer 610 has an opening 612 at one end and that is aligned with the second opening 544 in the fluid path 540 within the base connector 500 (e.g., to create fluid communication between the fluid path 540 and the film based fluid path 600). The middle layer 620 has a channel 622 extending along a portion of its length and the top/upper layer 630 is located on the middle layer 620 and covers the channel 622. During fluid transfer to the patient, the fluid may pass through the channel 622 and the opening 612 and into the fluid path 540 within the base connector 500. Conversely during transfer of fluid from the patient, fluid may flow from the fluid path 540 in the base connector 500, through the opening 612 and into the channel 622.

Although a film based extension set/fluid path way and a standard extension set/tube are shown and discussed above, other embodiments may be connected to other extension sets. For example, the base connector may be connected to a sensing extension set, a bifurcated extension set, a medical article extension set, or any other type of extension set. Additionally, although the Figures show the tube 700 and film based fluid pathway 600 in conjunction with the dressing 570, other embodiments may have the dressing without the tube 700 and film based fluid pathway 600 or the tube 700 and film based fluid pathway 600 without the dressing 570 (e.g., the film based fluid pathway 600 may be part of or independent from the dressing 570).

FIGS. 13 and 14 schematically show cross-sectional views of the catheter hub 200 and the base connector 500 (with a film based fluid path 600) when the base connector 500 is connected. As can be seen, when the base connector 600 is located within the intermediate portion 250 of the catheter hub 200, the biasing member/element 310 biases the base connector 500 toward the distal end 240 of the catheter hub 200. This, in turn, biases the first opening 542 of the base connector fluid path 540 toward the inlet 262 of the catheter hub flow path 260 and seals the sealing element 550 against the fluid seal interface 300 and/or the flanged portion 212 of the catheter 210. In embodiments in which the sealing element 550 seals against the flanged portion 212 of the catheter 210, the catheter hub 200 (e.g., the body 210) may be isolated from the fluid passing through the device 100 (i.e. the material(s) used to construct the catheter hub 200 are not in contact with the fluid).

To help prevent retrograde blood flow through the catheter system 100, the system 100 may include a valve mechanism 89 that selectively allows and prevent fluid flow through the device 100. For example, as shown in FIG. 14, the base connector 500 may include a two way pressure activated valve 580 (e.g., a slit diaphragm type structure) located within the fluid path 540 or adjacent the first opening 542. In the presence of a large enough pressure (e.g., above the retrograde venous pressure of the patient in a reverse direction and/or above a smaller pressure in a forward direction), the valve 580 will open to allow fluid flow through the device 100. In some embodiments, the valve 580 may be integral with the sealing element 550. Alternatively, the base connector 500 may not have a separate sealing element 550 and the valve 580 may act as the sealing element (e.g., the valve 580 may seal against the fluid seal interface 300).

In some embodiments, an introducer 800 may be used to insert the catheter 210 into the patient's vein. As shown in FIGS. 17-20, the introducer 800 may have an introducer body 810 (e.g., a handle) and one or more jaw members 820 that may move relative to the body 810 (e.g., from a first position to a second position), for example, about a hinge 822. Each of the jaw members 820 may be sized and shaped to be received by the intermediate portion 250 and the indents 254 of the catheter hub 200 and may have a snap retention feature 824 to receive the snap tabs 280 located on the catheter hub 200. The introducer 800 also includes a needle 830 that is sized to extend through the flow path 260 in the catheter hub 200 and/or the catheter 210.

Figure 18:
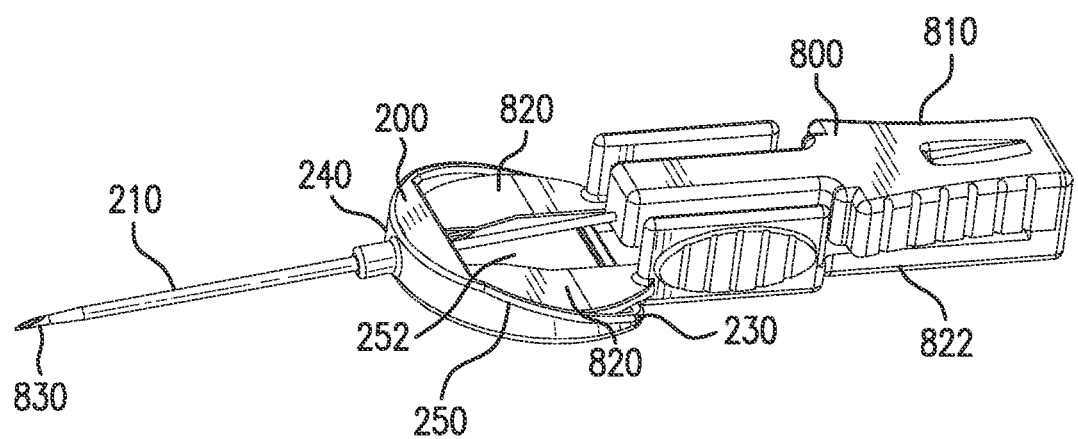
FIGS. 18 and 19 schematically show various views of the introducer connected to the catheter hub, in accordance with some embodiments of the present invention.
Figure 19:
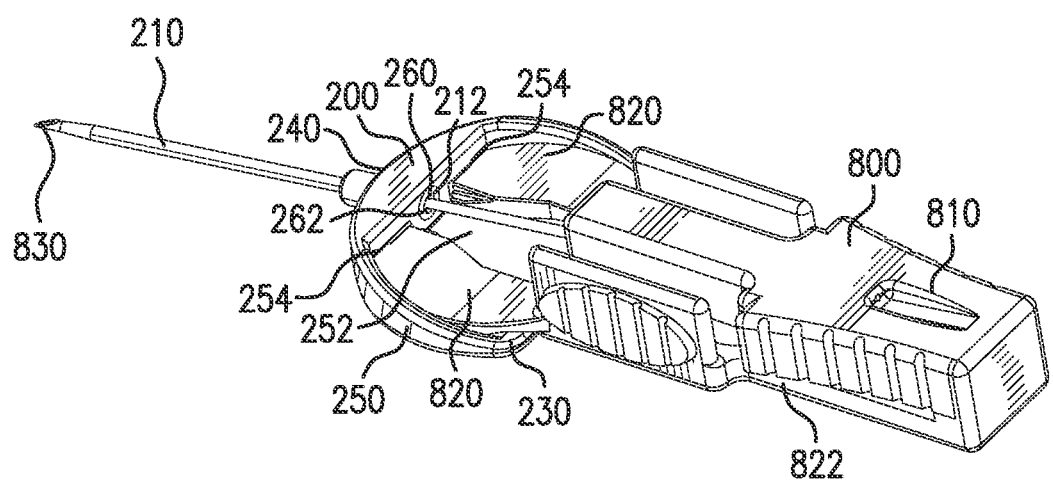
Figure 20:
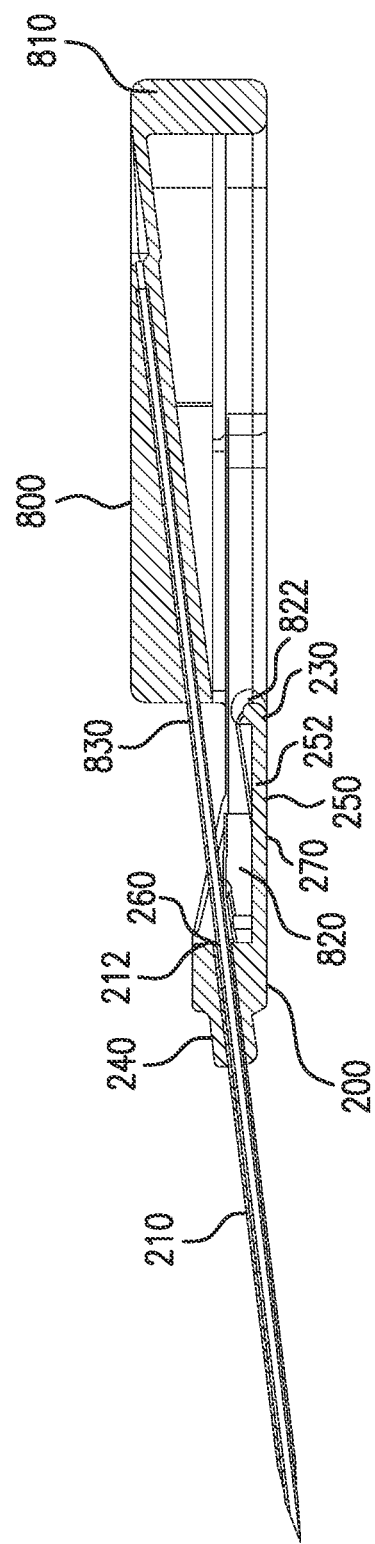
FIG. 20 schematically shows a cross-sectional view of the introducer connected to the catheter hub, in accordance with various embodiments of the present invention.

To that end and to connect the introducer 800 to the catheter hub 200, the manufacturer may insert the tip of the needle 830 into the inlet 262 of the flow path 260 and the catheter 210 and then press the jaw members 820 into the intermediate portion 250 causing the jaw members 820 to enter the indents 254, the snap tabs 280 to enter the snap retention features 824, and the needle to extend through the remainder of the flow path 260 and catheter 210 (FIG. 18-20). When the introducer 800 is connected to the catheter hub 200, the user may now insert the needle 830 into the patient's vein and place the stabilization surface 270 on the patient. If equipped, the user may then use the adhesive on the stabilization surface 270 to secure the catheter hub 200 to the patient.

Once the hub 200 is in place and the catheter 210 is in the vein, the user may press inward on the jaw members 820 to release them from the snap tabs 280 and may disconnect the introducer 800 from the catheter hub 200. As the user disconnects the introducer 800, the needle 830 will be removed from the catheter 210, leaving the catheter 210 in place in the vein. In some embodiments, the catheter hub 200 may be equipped with a needle protection cover (e.g., a stainless steel stamped element) that captures the needle tip and disengages from the catheter hub 200 for safe sharps disposal.

After removal of the introducer 800, the base connector 500 may be connected to the catheter hub 200 as discussed above to fluidly connect the fluid path 540 within the base connector 500 to the flow path 260 and catheter 210 in the catheter hub 200. If the system 100 has a dressing 570, the user may remove the release liner 576 and secure the patch layer 572 (e.g., the securement portion 571 to the patient). The user may then transfer fluid to and/or from the patient via the catheter system 100.

It should be noted that various embodiments of the present invention provide numerous benefits over prior art catheter systems. For example, because the base connector 500 easily connects to the catheter hub 200 by essentially snapping it in place, there is no rotation between the connector and the catheter. This, in turn, eliminates undesirable rotation of any stabilizing structures (e.g., the structures that stabilize the device on the patient), allows the device to sit flat on the patient, and is more comfortable for the patient.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A low profile catheter system comprising:
   a catheter hub having a proximal end, a distal end, a stabilization surface located on an underside of the catheter hub and a receptacle located within a top surface of the catheter hub, the stabilization surface configured to stabilize the catheter hub on a patient, the catheter hub also having a substantially linear flow path extending from an opening at the distal end to an inlet located within an intermediate portion of the catheter hub, the flow path configured to allow fluid to flow between the distal end and the intermediate portion of the catheter hub, the inlet of the flow path located between the proximal end and the distal end of the catheter hub, the catheter hub also having a fluid seal interface around the inlet of the flow path; and
   a base connector having a fluid path extending through at least a portion of the base being located connector and between a first opening and a second opening, the receptacle being located within the intermediate portion of the catheter hub and being configured to receive the base connector such that the base connector, the first opening, the second opening and the fluid path are located within the receptacle, the fluid path being fluidly connected to the inlet of the flow path in the catheter hub when the base connector is received by the receptacle within the intermediate portion of the catheter hub, the first opening of the fluid path is biased toward the fluid seal interface.

2. The low profile catheter system of claim 1, further comprising:
   a catheter at least partially secured within and extending into the flow path.

3. The low profile catheter system of claim 2, wherein at least a portion of the underside includes a flat surface, the catheter having a longitudinal axis oriented at an angle with respect to the flat surface.

4. The low profile catheter system of claim 2, further comprising:
   an introducer configured to removably connect with the catheter hub when the base connector is not connected, the introducer having a handle and a needle configured to extend through the flow path and catheter when the introducer is connected.

5. The low profile catheter system of claim 1, wherein the base connector includes a sealing member located at the first opening of the fluid path, the sealing member configured to seal against the fluid seal interface when axially biased toward the fluid seal interface.

6. The low profile catheter system of claim 1, further comprising:
   a first retention feature located on the catheter hub; and
   a second retention feature located on the base connector, the first and second retention features configured to interact with one another to secure the base connector to the catheter hub when the base connector is received by the intermediate portion of the catheter hub.

7. The low profile catheter system of claim 1, wherein the catheter hub has at least one indent and the base connector includes at least one projection extending from the base connector, the at least one projection configured to enter the at least one indent in the catheter hub upon receiving the base connector to align the base connector within the catheter hub.

8. The low profile catheter system of claim 1, wherein the catheter hub includes at least one opening extending therethrough, the at least one opening configured to provide access to the patient's skin.

9. The low profile catheter system of claim 1, wherein the base connector further includes a valve mechanism configured to control fluid flow through the fluid path.

10. The low profile catheter system of claim 9, wherein the valve mechanism includes a two-way pressure activated valve.

11. The low profile catheter system of claim 1, wherein a bottom surface of the base connector includes at least one recess, the at least one recess configured to house at least one sensor.

12. The low profile catheter system of claim 1, further comprising an adhesive layer located on the stabilization surface and configured to secure the catheter hub to the patient.

13. The low profile catheter system of claim 1, further comprising a tube connected to the second opening of the fluid path.

14. The low profile catheter system of claim 1, further comprising a dressing secured to the base connector, the dressing configured to secure the catheter system to the patient.

15. The low profile catheter system of claim 14, wherein the dressing includes:
   a patch layer secured to a top surface of the base connector, the patch layer having a securement portion extending beyond the top surface of the base connector and configured to adhere to the patient.

16. The low profile catheter system of claim 15, wherein the dressing further includes
   a first film layer located at least partially on the patch layer and having an opening nearer a first end of the first film layer,
   a second film layer located on the first film layer and having a channel extending along at least a portion of a length of the second film layer, and
   a third film layer located on the second film layer; the first, second and third film layers, the opening in the first film layer, and the channel forming a fluid pathway, the fluid pathway in fluid communication with the fluid path within the base connector.

17. The low profile catheter system of claim 1, wherein the catheter hub includes at least one projection extending from a surface of the catheter hub and the base connector includes at least one recess, the at least one projection entering the at least one recess when the base connector is received by the catheter hub, thereby securing the base connector to the catheter hub.

* * * * *

UNITED STATES PATENT AND TRADEMARK OFFICE
CERTIFICATE OF CORRECTION

| | |
|---|---|
| PATENT NO. | : 11,565,084 B2 |
| APPLICATION NO. | : 16/864374 |
| DATED | : January 31, 2023 |
| INVENTOR(S) | : Todd Chelak et al. |

It is certified that error appears in the above-identified patent and that said Letters Patent is hereby corrected as shown below:

In the Claims

In Claim 1 (Column 9, Line 31, please replace "at least a portion of the base being located connector and between a first opening and a second opening," with -- at least a portion of the base connector and between a first opening and a second opening, --

Signed and Sealed this
Fourth Day of April, 2023

Katherine Kelly Vidal
*Director of the United States Patent and Trademark Office*